United States Patent
Anand et al.

[11] Patent Number: 5,864,331
[45] Date of Patent: Jan. 26, 1999

[54] SHIELDING SYSTEM AND METHOD FOR AN ENTERTAINMENT SYSTEM FOR USE WITH A MAGNETIC RESONANCE IMAGING DEVICE

[75] Inventors: Prem K. Anand, Roswell, Ga.; Stephen Samuel Trani, Virginia Beach, Va.

[73] Assignee: General Electric Company, Milwaukee, Wis.

[21] Appl. No.: 843,867

[22] Filed: Apr. 17, 1997

Related U.S. Application Data

[63] Continuation of Ser. No. 514,849, Aug. 14, 1995.

[51] Int. Cl.⁶ .............................. G09G 5/34; H04N 5/64; H05K 9/00
[52] U.S. Cl. .......................... 345/126; 345/905; 348/794; 361/816
[58] Field of Search ............................ 345/905; 348/818, 348/819, 820, 836, 794, 77; 206/719; 257/659, 422; 307/91; 315/85; 349/59; 361/800, 816; 600/410; 174/35 R; 505/872

[56] References Cited

U.S. PATENT DOCUMENTS

| | | | |
|---|---|---|---|
| 4,246,613 | 1/1981 | Choder et al. | 348/819 |
| 4,554,638 | 11/1985 | Iida | 364/521 |
| 4,570,158 | 2/1986 | Bleich et al. | 340/727 |
| 4,696,030 | 9/1987 | Egozi | 379/167 |
| 4,785,136 | 11/1988 | Mollet et al. | 174/35 R |
| 4,804,261 | 2/1989 | Kirschen | 351/158 |
| 4,853,791 | 8/1989 | Ginther, Jr. | 348/819 |
| 4,901,141 | 2/1990 | Costello | 358/93 |
| 5,043,529 | 8/1991 | Vanesky et al. | 174/35 R |
| 5,076,275 | 12/1991 | Bechor et al. | 128/653.2 |
| 5,192,893 | 3/1993 | Velasco et al. | 315/85 |
| 5,323,298 | 6/1994 | Shatas et al. | 361/816 |
| 5,432,544 | 7/1995 | Shatas et al. | 361/816 |
| 5,436,803 | 7/1995 | Annis et al. | 174/35 R |
| 5,464,014 | 11/1995 | Sugahara | 345/1 |
| 5,514,833 | 5/1996 | Kuth | 174/35 R |

*Primary Examiner*—Jeffery Brier
*Assistant Examiner*—Paul A. Bell
*Attorney, Agent, or Firm*—Scott A. Horstemeyer; John H. Pilarski

[57] ABSTRACT

An entertainment system for use with a magnetic resonance imaging (MRI) device has a display panel and associated electronics which are mounted close to the MRI device and which are enclosed within a Faraday shield. A patient may be placed within the MRI device in a variety of positions and may view images from the display panel either directly or through a mirror, prism, or corner reflector. In order for the patient to view the images in the correct orientation regardless of the exact positioning, the display panel can display the images normally, with the images flipped from top to bottom, with the images flipped from left to right, and with the images flipped both from top to bottom and from left to right. The display panel is formed with a dark-colored focus area which forms a border around the display panel and which directs the attention of the patient toward the images on the display panel. The entertainment system indicates the various states of the MRI procedure through a set of lamps colored and arranged to simulate a typical traffic light. By using the traffic light configuration and coloring, patients can easily determine the state of the MRI procedure. The entertainment system calms the patient, distracts the patient from the MRI procedure, and makes it easier for the patient to remain still during the MRI procedure. As a result of the entertainment system, better quality images may be obtained with the MRI device.

9 Claims, 6 Drawing Sheets

SHIELDING SYSTEM AND METHOD FOR AN ENTERTAINMENT SYSTEM FOR USE WITH A MAGNETIC RESONANCE IMAGING DEVICE

The present application is a continuation application of co-pending application entitled "Entertainment System for Use with a Magnetic Resonance Imaging Device", filed on Aug. 14, 1995 and assigned Ser. No. 08/514,849.

BACKGROUND OF THE INVENTION

1. Field of the Invention

The present invention generally relates to an entertainment system and method and, more particularly, to an entertainment system and method for use with a magnetic resonance imaging device.

2. Description of the Prior Art

In the medical field, magnetic resonance imaging (MRI) is a commonly used non-invasive technique to diagnose the medical condition of a patient. Typically, the patient is placed within a large homogeneous magnetic field and is subjected to a set of gradient fields and RF fields. The various fields are accurately controlled to cause nuclei within a selected slice of the patient to precess about an axis and to emit RF signals. These signals are then used to reconstruct an image of the slice. By varying the gradient fields, images of the patient at different slices may be captured. The separate slices can then be combined to form a complete scan of the patient.

A typical MRI device is designed to have a central bore within which the patient is inserted. This bore is fairly small and may induce claustrophobic feelings in the patient. As is known in the art, these claustrophobic feelings may be reduced or eliminated by providing the patient with some type of entertainment.

A problem with providing the patient with some type of entertainment is that very small magnetic fields generated by another device can destroy the images generated by the MRI device. Conversely, the strong fields generated by the MRI device may prevent the normal operation of certain devices, such as a cathode ray tube (CRT) or liquid display panel (LCD), within the vicinity of the MRI device. Therefore, any type of system used to entertain the patient must not generate any stray magnetic fields in the vicinity of the MRI device and should be shielded from the magnetic fields generated by the MRI device.

Despite these constraints, many types of systems have been designed to provide the patient with some entertainment thereby distracting the patient from the MRI procedure. In order to isolate the entertainment systems from the fields generated by the MRI device and to prevent any magnetic fields from effecting the MRI device, some systems pipe in video images to the patient while the patient is within the MRI device. For instance, U.S. Pat. No. 4,901,141 to Costello and U.S. Pat. No. 5,134,373 to Tsuruno et al. both disclose video systems in which video images are supplied through optic fibers to the patient. These systems are rather expensive to install since the MRI device must be retro-fitted with the optical fibers.

Rather than routing the video images by optical fiber, another type of entertainment system generates an image behind the MRI device and has a mirror for reflecting the image to the patient. For instance, a viewing system in U.S. Pat. No. 5,076,275 to Bechor et al. and an MRI video system disclosed in a Nuclear Associates brochure both reflect images generated from a display panel located behind the patient into the eyes of the patient. These systems may use a reflective surface mounted to the MRI device or reflective surfaces which are mounted onto goggles worn by the patient.

While these systems are easier to install than systems which route the video images through optical fibers, these systems do not readily accommodate different positions of the patient. For instance, while a patient is often in a supine position, the MRI procedures vary in whether the patient is placed in a supine position or prone position or whether the patient is placed head-first or feet-first within the MRI device. The conventional entertainment systems cannot accommodate all of the different positions that a patient may be placed and, at most, may be able to accommodate only a single position of the patient. It is therefore a problem with conventional entertainment systems which are used with MRI devices to provide video images to the patient for a variety of positions.

Also, with many of the existing MRI entertainment systems, the patient may find it difficult to focus on the video images and may therefore find it difficult to completely relax. This may be especially true for the entertainment systems which reflect the video images from behind the MRI device to the patient. With this type of entertainment system, the patient may be distracted by items which are adjacent to the display screen or by people working behind the patient. It would therefore be desirable to have the patient focus on the video images during the MRI procedure so that the patient is able to relax.

In order for the MRI device to produce high resolution images of the patient, the patient must remain as still as possible while the MRI device is operating. While the entire procedure may last more than an hour in duration, the MRI device is not imaging during the entire hour. Instead, the procedure is usually comprised of two or more imaging sequences with pauses in between the sequences. During these pauses between sequences, the patient can relax and may move about a minimal amount.

The status of the MRI procedure, such as when the MRI device is imaging or pausing, may be indicated to the patient in a variety of ways. One manner of indicating the states of the MRI procedure is by simply verbally informing the patient of whether the MRI device is imaging, pausing, or about to image. A better way, disclosed in JP-A-145643, is to flash a colored light to warn the patient that an imaging sequence is about to begin and to steadily illuminate the MRI device with the colored light for the period during which the MRI device is imaging.

A still better way, disclosed in U.S. Pat. No. 5,355,885 to Tsuda et al., provides the patient with information about the particular operation that is occurring. With the system disclosed by Tsuda et al., the inspection space within the MRI device is illuminated with a number of colors to indicate the different operations. This system illuminates the inspection space with a mixture of green and yellow light and then illuminates the space with just a yellow light during a pretreatment period. A red light flashes before the beginning of an imaging sequence and then the green light illuminates the space during the imaging sequence. As the imaging sequence progresses, the space is illuminated with a mixture of both green and yellow lights with the mixture slowly changing to entirely yellow to indicate the end of the imaging sequence. As with the beginning of the MRI procedure, the end of the entire procedure is indicated with the mixture of green and yellow lights.

While the system disclosed in Tsuda et al. can indicate the various states of the MRI device, it may be difficult for many patients to determine the exact state of the MRI device. The patient may be in a state of anxiety and may not remember the exact relationship between the colors and the states of the MRI device. Also, many patients may have trouble distinguishing a slight mixture of colors, such as green and yellow, from a pure color of light, such as just yellow. Consequently, some patients may determine that the MRI device is pausing when in fact the MRI device is still acquiring images. It is therefore a problem to accurately and reliably indicate the various states of the MRI procedure to a patient.

SUMMARY OF THE INVENTION

An object of the present invention is to reliably and accurately indicate the various states of an MRI procedure to a patient.

Another object of the present invention is to calm a patient by providing video images during an MRI procedure.

Another object of the present invention is to provide a low cost system for entertaining a patient.

Another object of the present invention is to provide video images to a patient for a number of different positions in which the patient may be placed within an MRI device.

Additional objects, advantages, and novel features of the invention will be set forth in the description which follows, and will become apparent to those skilled in the art upon reading this description or practicing the invention.

To achieve the foregoing and other objects, a novel entertainment system for use with a magnetic resonance imaging (MRI) device receives video data and has a mode selector for placing the entertainment system into any one of a plurality of modes. A data processor alters the sequence of the video data according to the mode selected, with each mode associated with a different sequence of data. A display panel generates a video image based on the sequence of video data supplied from the data processor with the orientation of the video image on the display panel being different for each of the different modes. The mode of the entertainment system is selected according to the position of a patient within the MRI device so that the video image will appear to be in its normal orientation from the patient's viewing position.

In the preferred embodiment, the patient may be positioned head-first or feet-first within the MRI device and may be in a supine or prone position. Additionally, the video image may be reflected off of a mirror, prism, or corner reflector before reaching the eyes of the patient. To accommodate these different viewing positions, the entertainment system has the different modes in which the image may be unaltered, may be flipped from top to bottom, may be flipped from left to right, or may be flipped both from top to bottom and from left to right.

An entertainment system, according to a second aspect of the invention, receives video data, such as from a TV, cable TV, VCR, etc., and has a display panel for generating a digital image. A focus area is formed completely around the display panel and has a surface area greater than the surface area of the display panel. The focus area has a dark color and helps to direct a gaze of a patient within the MRI device to the video image on the display panel. By focusing the attention of the patient onto the display panel, the patient becomes distracted, relaxed, and is better able to remain still during an imaging sequence. Since the patient is better able to remain still, the entertainment system of the invention can improve the quality of images acquired by the MRI device.

In a third aspect, the invention relates to a system for indicating the various states of an MRI device to a patient. The indicating system comprises a red lamp, a yellow lamp, and a green lamp arranged in a traffic light configuration so that the yellow lamp is located directly beneath the red lamp and the green lamp is located directly beneath the yellow lamp. The system further has first, second, and third driving circuits for respectively driving the red, yellow, and green lamps. The first, second, and third driving circuits are activated in accordance with an imaging sequence of the MRI device so that the green lamp is activated when the MRI device is inactive, the red lamp is activated when the MRI device is acquiring images of the patient, and the yellow lamp is activated before the MRI device begins to acquire the images of the patient and is activated for a predetermined period of time. The traffic light configuration of the red, yellow, and green lamps permits the patient to easily determine the states of the MRI device even when the patient is in a state of anxiety or has feelings of claustrophobia.

In a fourth aspect, the invention relates to a method of providing images to a patient during a magnetic resonance imaging procedure. The method comprises the steps of receiving video data at an input terminal of an entertainment system and placing the entertainment system into one of a plurality of modes. The sequence of the digital video data is controlled based upon the selected mode, with each mode associated with a unique sequence of digital video data. A video image is generated on a display panel based on the controlled sequence of digital video data. The mode of the entertainment system is selected based on a position of the patient within the MRI device so that the patient can view the video image in its normal orientation.

In a fifth aspect, the invention relates to a method for indicating the various states of an MRI device to a patient. The method comprises the steps of arranging a red lamp, a yellow lamp, and a green lamp in a traffic light configuration with the yellow lamp located directly beneath the red lamp and the green lamp located directly beneath the yellow lamp. The green lamp is activated when the MRI device is inactive, the red lamp is activated when the MRI device is acquiring images of the patient, and the yellow lamp is activated before the MRI device begins to acquire images of the patient and is activated for a predetermined period of time. The arrangement of the red lamp, yellow, and green lamps in the traffic light configuration permits the patient to easily determine the states of the MRI device.

BRIEF DESCRIPTION OF THE DRAWINGS

The accompanying drawings, which are incorporated in, and form a part of, the specification, illustrate a preferred embodiment of the present invention and, together with the description, serve to explain the principles of the invention. The drawings are not necessarily to scale, emphasis instead being placed upon clearly illustrating the principles of the invention. In the drawings.

DETAILED DESCRIPTION OF THE PREFERRED EMBODIMENT

Figure 1:
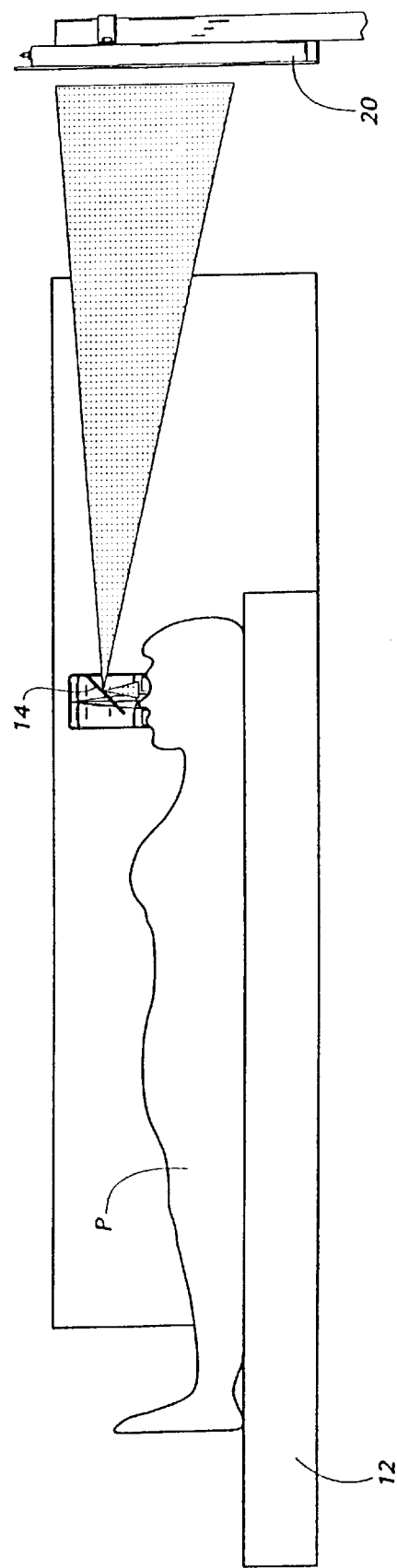
FIG. 1 is a side view of a patient within an MRI device having an entertainment system according to a preferred embodiment of the invention.

Reference will now be made in detail to the preferred embodiment of the invention. With reference to FIG. 1, an entertainment system according to the invention is shown with a magnetic resonance imaging (MRI) device in which a patient P is placed upon a moveable bed 12. An image or set of images are generated by a display panel 20 and may be reflected off of a mirror, prism, or corner reflector 14 into the eyes of the patient P. As is known in the industry, these images can distract the patient P from the MRI procedure and help the patient P to relax. By distracting and relaxing the patient P, the patient P is able to remain still for longer periods of time, which permits the MRI device to obtain better quality images.

Figure 2:
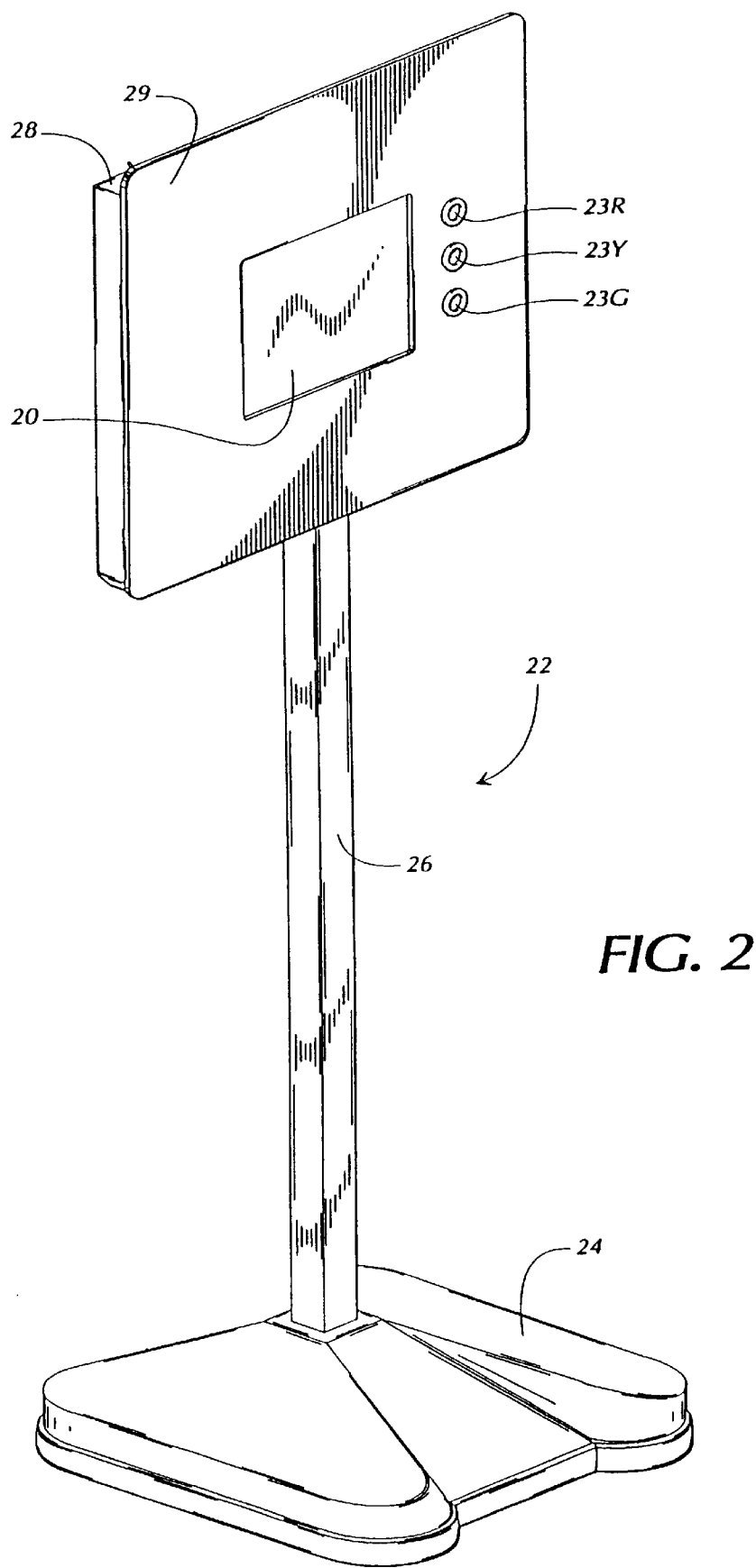
FIG. 2 is a perspective view of a stand for holding a display panel forming part of the entertainment system of the invention.

The display panel 20 may be positioned relative to the MRI device in a number of different ways, such as mounting the display panel 20 directly onto a wall behind or in front of the MRI device or incorporating the display panel 20 within a stand, such as stand 22 shown in FIG. 2. The stand 22 has a base 24, a vertical extension member 26, and a shielding enclosure 28 for housing the display panel 20. While not shown, the vertical extension member 26 is adjustable so that the display panel 20 may be placed at different heights.

The preferred distance for placing the display panel 20 and stand 22 relative to the MRI device will depend upon a number of factors, including the size of the display panel 20. In the example disclosed, the display panel 20 has a diagonal length of 10.4 inches and is placed at any suitable distance to the MRI device, typically in the range of about 3 to 5 feet from the MRI device. It should be understood that the display panel 20 may have a different size and that the display panel 20 may be placed at other distances from the rear of the MRI device.

The display panel 20 preferably has a number of indicator lamps 23 for indicating the various states of the MRI procedure. The lamps 23 are comprised of a red lamp 23R, a yellow lamp 23Y, and a green lamp 23G arranged along a vertical column. The lamps 23 are energized so that the green lamp 23G is lit to indicate that the MRI device is inactive, the yellow lamp 23Y is lit to indicate that an imaging sequence is about to begin, and the red lamp 23R is lit to indicate that the MRI device is acquiring images of the patient P.

The colors of the lamps 23 and the arrangement of the lamps 23 are specifically designed to simulate the appearance and operation of a typical traffic light. When the green lamp 23G is lit, the patient P knows that the MRI device is inactive and that he or she is able to "go" or move to different locations. On the other hand, when the red lamp 23R is lit, the patient P knows that the MRI device is acquiring images and that he or she must "stop" all motion and remain as still as possible. The yellow lamp 23Y, similar to the traffic light, warns the patient P that he or she will soon have to "stop" all motion.

The traffic light configuration and selection of colors for the lamps 23 clearly and simply indicate the various states of the MRI device to the patient P. Most patients P, even those who may be too young to drive, understand that green means go, that red means stop, and that yellow is a warning light. Most patients P can therefore easily determine whether he or she can move about based upon the signals from the lamps 23. Thus, even when a patient P is in a heightened state of anxiety or has feelings of claustrophobia, the patient P should still be able to determine the states of the MRI device.

In addition to the lamps 23 and the display panel 20, the shielding enclosure 28 also has a focus area 29. The focus area 29 forms a border completely around the perimeter of the display panel 20 and comprises a substantial portion of the front surface of the shielding enclosure 28. By placing the display panel 20 within a large focus area 29, the gaze from a patient P is directed toward the center of the focus area 29 and onto the display panel 20. Thus, the focus area 29 directs the attention of the patient P toward the images generated by the display panel 20.

The focus area 29, in addition to having a proportionately large amount of surface area on the face of the shielding enclosure 28, is also selected to have a dark color, preferably black. A dark focus area 29 increases the amount of contrast between itself and the images on the display panel 20 and, consequently, further directs the gaze from the patient P onto the display panel 20. An overall effect of the focus area 29 is to direct the patient's P attention to the video image thereby relaxing the patient P and relieving feelings of anxiety or claustrophobia. Thus, with the focus area 29, the patient P can more easily remain still during the MRI procedure.

Figure 3:
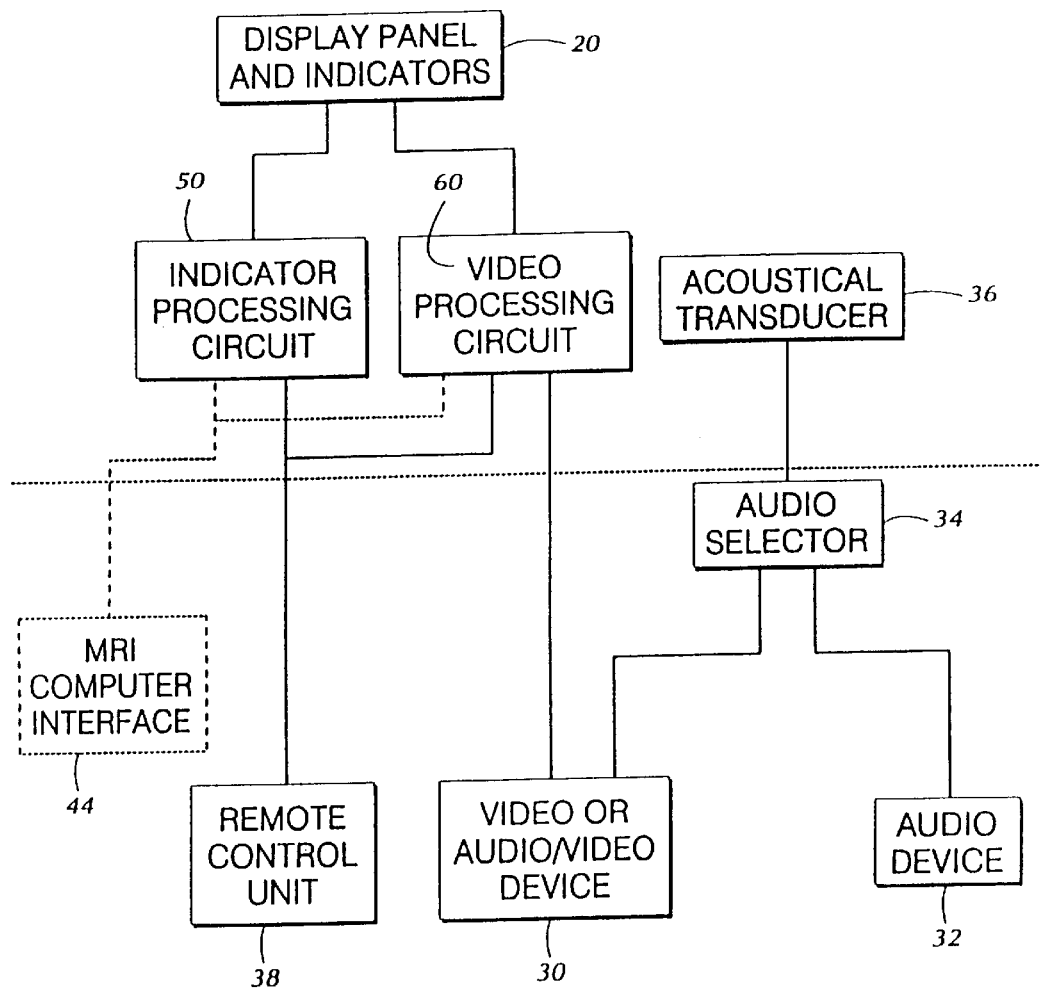
FIG. 3 is a block diagram of the entertainment system according to a preferred embodiment.

A block diagram of the entertainment system is shown in FIG. 3. The entertainment system comprises at least one video or audio/video device 30 for producing video signals that are sent to a video processing circuit 60. When the video device 30 is an audio/video device 30, the audio signals from the device 30 are supplied to an audio selector 34. The invention may use any type of video or audio/video device 30. Thus, for example, the device 30 may be a laser disc player, a video cassette recorder (VCR), or an output from a cable television system.

The entertainment system may additionally have at least one audio device 32 which supplies its audio signals to the audio selector 34. The audio selector 34 passes only one of the audio signals supplied at its inputs to an acoustical transducer 36 which converts the signals into sound.

The invention is not limited to any specific type of audio device 32, audio selector 34, or acoustical transducer 36 and any suitable components may be used. For instance, the audio device 32, audio selector 34 and acoustical transducer 36 may be those disclosed in U.S. Pat. No. 5,076,275 to Bechor et al., the disclosure of which is incorporated by reference. The audio device 32 may comprise a tape deck, CD player, or tuner and the audio selector 34 may be a separate device, such as a simple switch, or may be incorporated within another audio device 32, such as the tuner. The acoustical transducer 36 may comprise a loudspeaker and/or may comprise a headphone operable within the bore of the MRI device.

The video processing circuit 60 can drive the display panel 20 in any one of four modes which are selected according to the position of the patient P within the MRI device. In a first mode, when the patient P is head-first within the MRI device and is in a prone position, the video processing circuit 60 drives the display panel 20 in a normal viewing format so that the images from the display panel 20 may be directly viewed by the patient P without any mirror 14. In other words, when the patient P looks at the display panel 20 directly, the images from the display panel 20 are positioned normally both from left to right and from top to bottom.

The video processing circuit 60 drives the display panel 20 in a second mode when the patient P is head-first within the MRI device, is in a supine position, and receives the video images from the mirror 14. When the patient P is in this position, the video processing circuit 60 drives the display panel 20 so that the images are flipped from left to right.

In a third mode, the patient P is head-first within the MRI device, is supine, and views images from the display panel 20 without the mirror 14. In order for the patient P to view the image in their correct orientation, the video processing circuit 60 drives the display panel 20 so that the images are flipped from top to bottom.

Finally, when the patient P is feet-first within the MRI device, is in a supine position, and views the images from the display panel 20 with the mirror 14, which is the position shown in FIG. 1(A), the video processing circuit 60 drives the display panel 20 in a fourth mode. In this mode, the images from the display panel are flipped from top to bottom and are flipped from left to right. Thus, when the patient P views these images through the mirror, the images from the display panel 20 will appear in their normal orientation.

Figure 4:
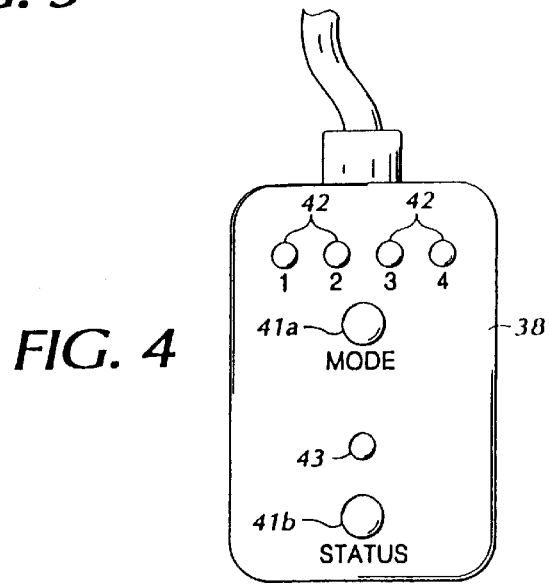
FIG. 4 is a top view of an exemplary remote control unit shown in FIG. 3.

The entertainment system also comprises a remote control unit 38 which sends signals to both an indicator processing circuit 50 and to the video processing circuit 60. With reference to FIG. 4, in the preferred embodiment the remote control unit 38 comprises a manually activated unit having two buttons 41a and 41b, four indicators 42 for video processing, and one indicator 43 for indicator or status processor. The button 41b is depressed by an MRI operator before the beginning of an imaging sequence. The indicator processor circuit 50 lights the yellow lamp 23Y for a predetermined period of time and then lights the red lamp 23R to indicate that all motion must "stop". At the end of the imaging sequence, the MRI operator presses the button 41b again to cause the indicator processor circuit 50 to light the green lamp 23G to indicate that the patient P is free to move about.

The other button 41a is associated with four video indicators 42 and is for placing the display panel 20 in one of the four display modes. The MRI operator therefore only needs to depress the button 41a and toggle through until the indicator 42 lit corresponds to the position of the patient P in order for the images from the display panel 20 to be orientated correctly relative to the patient P. Preferably, the indicators 42 are light emitting diodes (LED) to indicate the four orientations and the LED associated with a selected orientation is energized in order to indicate the selected mode. Rather than manually depressing the buttons 41, both the indicator processing signals and orientation mode signal can be automatically produced by the MRI computer system and sent over a serial link, through an MRI computer interface 44, and to the indicator processing circuit 50 and the video processing circuit 60.

Figure 5A:
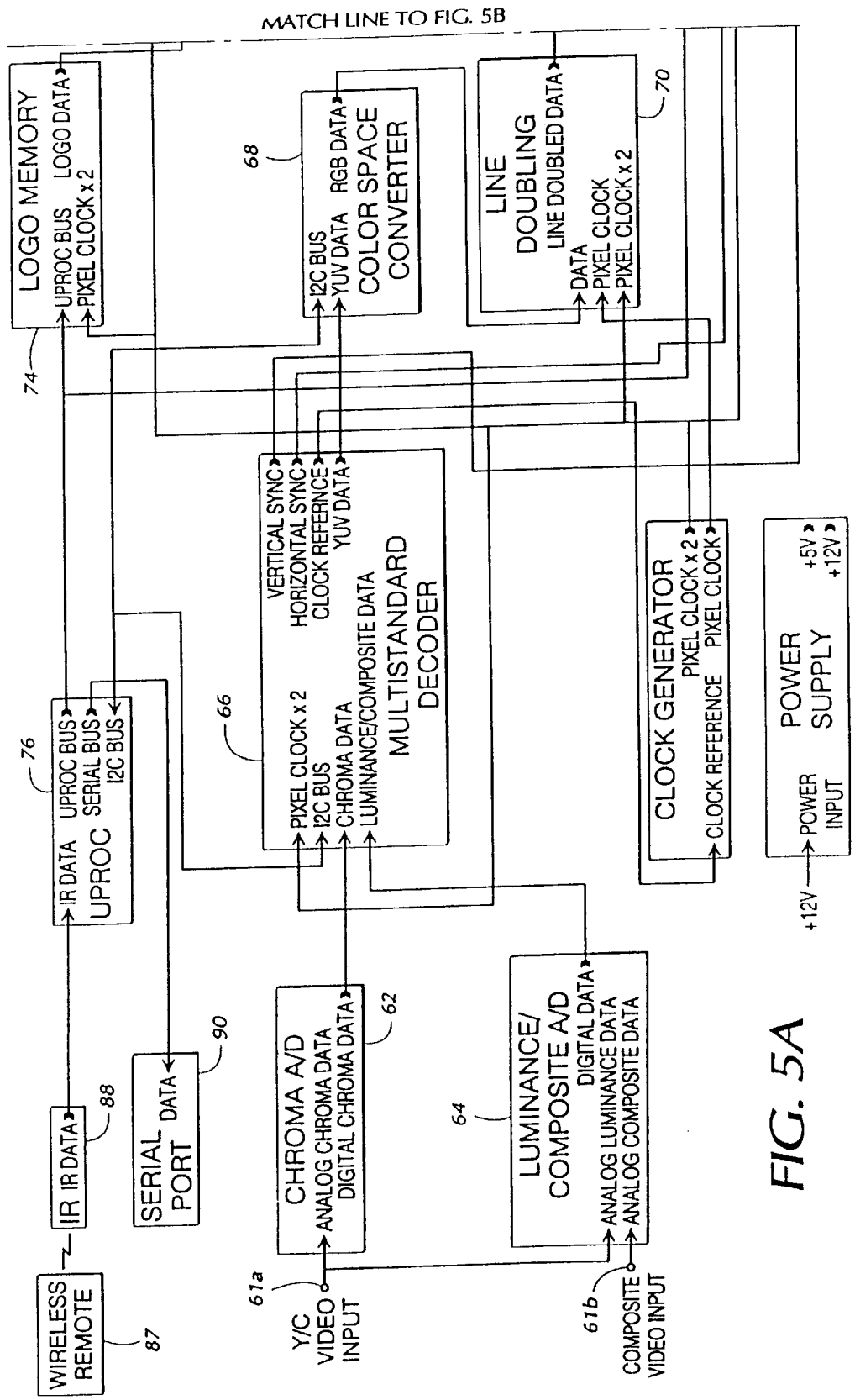
FIGS. 5A and 5B are block diagrams of a video processing circuit and indicator processing circuit shown in the entertainment system of FIG. 3.
Figure 5B:
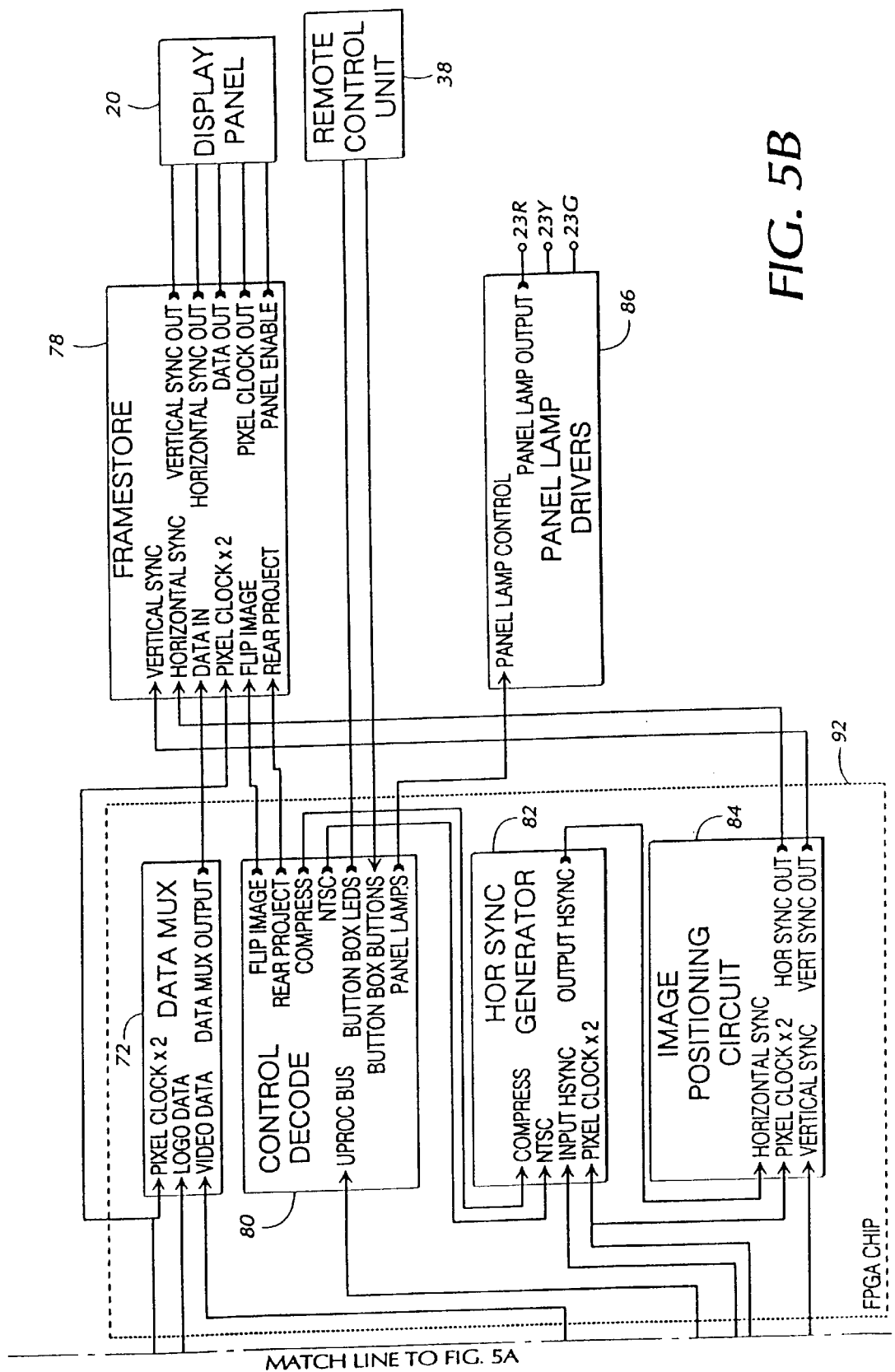

FIGS. 5A and 5B depict an example of the indicator processing circuit 50 and the video processing circuit 60. The video processing circuit 60 can receive video signals in a number of different formats and receives the video signals at either terminal 61a or 61b, depending upon the particular format of the video signal. If the video device 30 outputs signals as separate chroma C and luminance Y signals, the chroma C and luminance Y signals are input at terminal 61a and are respectively routed to a chroma analog-to-digital (A/D) converter 62 and to a luminance input at a luminance/composite A/D converter 64. If the video device 30 instead outputs signals as a composite video signal, then this composite video signal is routed to a composite input at the luminance/composite A/D converter 64.

The digital outputs from the chroma A/D converter 62 and the luminance/composite A/D converter 64 are supplied to a multi-standard decoder 66. The multi-standard decoder 66 determines the type of video signal that is being input to the video processing circuit 60 and preferably determines whether the video signals are in the NTSC format, the PAL format, or the SECAM format. The multi-standard decoder 66 reformats the chroma and luminance data and outputs the video data in a Y, U, and V data format. The Y, U, and V data from the multi-standard decoder 66 is input to a color space converter 68 which separates the data into red R, green G, and blue B digital data.

The red R, green G, and blue B digital data are output from the color space converter 68 and are input into a line doubling circuit 70. The display panel 20 is preferably an LCD panel having 480 rows of pixels. Since the video signals only have about 240 lines of data, the line doubling circuit 70 must double the number of lines in order for the signals to be formatted for the LCD panel 20. The video signals arrive in an interlaced format with the data for even lines being alternated with the data for the odd lines. The line doubling circuit 70 converts the interlaced data format into a progressive scan format compatible with the LCD panel 20 by doubling both the data for the even lines and the data for the odd lines and alternately supplying the even and odd data to a data multiplexer 72.

In addition to receiving the doubled line data from the line doubling circuit 70, the data multiplexer 72 also receives another input from memory 74. The memory 74 stores an image or a number of images which may be displayed on the display panel 20. For instance, the memory 74 may store a logo or banner for Health Images or may be a logo custom designed for the particular office operating the MRI device. The images from the memory 74 are routed through the data multiplexer 72 and ultimately to the display panel 20 only when the video processing circuit 60 is not receiving any video signals from the video device 30. Thus, the signals from the video device 30 take precedent over the images stored in memory 74.

A microprocessor 76 controls the data multiplexer 72 so that the images from the memory 74 are displayed only when the video device 30 is inactive. While not shown, the microprocessor 76 has access to memory including, but not limited to, RAM, ROM for storing software, and a hard drive. The microprocessor 76 is informed by the multi-standard decoder 66 whether video signals are being input from a video device 30. Thus, when video signals are not being input to the multi-standard decoder 66, the microprocessor 76 will control the data multiplexer 72 so that it outputs the video image stored in memory 74.

A framestore 78 receives the output from the data multiplexer 72 and has an output which drives the LCD panel 20. The framestore 78 is comprised of a block of video RAM which temporarily stores the video data before being displayed on the display panel 20. The framestore 78 can change the order of the video data so that the display panel 20 projects a video image in any one of the four modes. To control the sequence of the video data, the framestore 78 has a control input FLIP IMAGE for flipping the image from top to bottom and a REAR PROJECT control input for rotating the image from left to right.

The framestore 78 may be conceptualized as an array of data spaces. Without any control signals, the framestore 78 will store lines of data from the top to the bottom of the data array and from the left to the right of the data array. When the framestore 78 receives a control signal on the FLIP IMAGE input, the lines of the video data input to the framestore 78 will instead be stored in a sequence from the bottom to the top of the data array. If the framestore 78 receives a control signal on the REAR PROJECT input, then the video data within each line will be stored from right to left of the data array. Since the video data is always output from the framestore 78 from the top to bottom of the data array and from the left to right of the array, the video data will appear to have been flipped from top to bottom if the FLIP IMAGE input was received and will appear to have been rotated from left to right if the REAR PROJECT input was received.

The multi-standard decoder 66 separates the horizontal sync signal from the received video signals and supplies the horizontal sync signal to certain components of the video processing circuit 60, such as the line doubling circuit 70 and horizontal sync generator 82. The horizontal sync generator 82 doubles the speed of the horizontal sync signal and outputs this doubled signal to an image positioning circuit 84.

The image positioning circuit 84 permits both horizontal and vertical positional adjustments of an image on the LCD panel 20. The image positioning circuit 84 receives the doubled horizontal sync signal from the horizontal sync generator 82 and adjusts the timing of the double horizontal sync signal to cause a corresponding adjustment in the horizontal position of the image on the display panel 20. Similarly, the image positioning circuit 84 receives a vertical sync signal from the multi-standard decoder 66 and adjusts the timing of this signal to cause a corresponding adjustment in the vertical position of the image on the display panel 20.

A control decode 80 receives information from the microprocessor 76 and controls a number of devices according to the information received. The information received from the microprocessor 76 includes information as to which one of the four modes the display panel 20 should be placed. After receiving this information, the control decode 80 will send appropriate control signals to the FLIP IMAGE and REAR PROJECT inputs on the framestore 78.

The microprocessor 76 also sends the control decode 80 values of the horizontal and vertical adjustments. The values of the horizontal and vertical adjustments of the image depend upon the type of video signal, such as PAL or NTSC, and are stored in memory accessible by the microprocessor 76. The microprocessor 76 is informed of the type of video signal by the multi-standard decoder 66 and then sends the appropriate values of the adjustments to the control decode 80, which relays the information to the image positioning circuit 84 for executing the positional adjustments.

The control decode 80 also receives information from the remote control unit 38. After a button has been pressed on the remote control unit 38, the control decode 80 relays the information as to which button has been pressed to the microprocessor 76. If one of the buttons for controlling the mode of displaying the video was depressed, then the microprocessor 76 sends signals through the control decode 80 to the remote control unit 38 for energizing the LED associated with the depressed button so that the selected mode is indicated to the MRI operator.

Through the control decode 80, the microprocessor 76 also controls the lamps 23 to indicate the present state of the MRI procedure. After the microprocessor 76 receives an indication from the control decode 80 that the button for the lamps 23 on the remote control unit 38 has been depressed, the microprocessor 76 commands the control decode 80 to activate the yellow lamp 23Y to warn the patient that an imaging procedure is about to begin. After the microprocessor 76 detects that a predetermined period of time has elapsed, the microprocessor 76 commands the control decode 80 to activate the red lamp 23R. At the completion of the imaging sequence, when the microprocessor 76 receives an indication through the control decode 80 that the button on the remote control unit 38 has been depressed again, the microprocessor 76 commands the control decode 80 to activate the green lamp 23G to let the patient P know that he or she is allowed to move.

In response to a command from the microprocessor 76, the control decode 80 sends an appropriate control signal to a set of panel lamp drivers 86. The set of panel lamp drivers 86 comprises first, second, and third drivers for the red, yellow, and green lamps 23, respectively. The panel lamp drivers 86 convert the digital 5 volt signal from the control decode 80 into a 12 volt power signal suitable for driving the 12 volt lamps 23.

Instead of or in addition to the remote control unit 38, the entertainment system may have a wireless remote control unit 87. The wireless remote control unit 87 transmits infrared signals to an IR circuit 88 which converts the optical signals into electrical signals and outputs digital data signals to the microprocessor 76. The wireless remote control unit 38 may have the same buttons which are on the remote control unit 38 and/or may have other buttons for controlling other aspects of the entertainment system.

A serial port interface 90 permits serial communication with the microprocessor 76. The serial port interface 90 may be used as a diagnostic tool to debug existing software or may be used to reprogram the microprocessor 76. The microprocessor 76 could also use the serial port interface 90 to receive serial commands from another device. For instance, the microprocessor 76 may be informed by the MRI device of when an imaging sequence is about to begin or when the sequence has ended. The microprocessor 76 could then automatically generate signals to the indicator processing circuit 50 and to the video processing circuit 60 without any operator intervention. With such a control unit, the MRI operator would not have to place the display panel 20 in the separate display modes and would not have to depress a button at the beginning or end of each imaging sequence.

The data multiplexer 72, the control decode 80, the horizontal sync generator 82, and the image positioning circuit 84 form part of a field programmable gate array (FPGA). The programming of the FPGA will be apparent from the above descriptions of the data multiplexer 72, control decode 80, horizontal sync generator 82, and image positioning circuit 84 and, accordingly, will not be described in any further detail.

Figure 6:
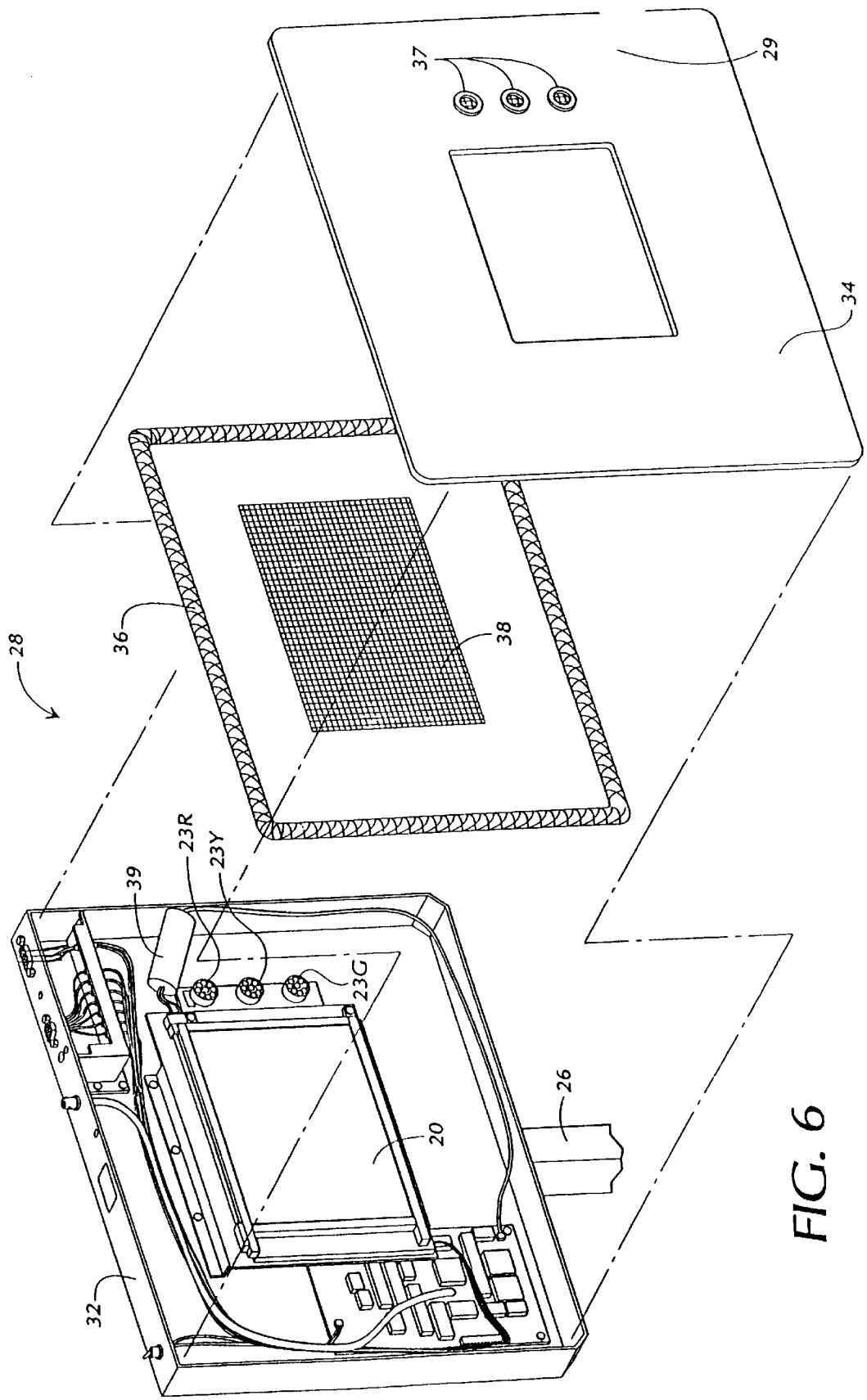
FIG. 6 is an exploded view of a shielding enclosure and display panel.

As discussed above, the display panel 20 must be shielded from the magnetic fields generated by the MRI device and the MRI device must be shielded from the magnetic fields generated by the display panel 20 and associated electronics. To accomplish this shielding, with reference to FIG. 6, the shielding enclosure 28 comprises a metal box 32, a metal cover plate 34 having the focus area 29, an RFI gasket 36, and a screen 38.

The display panel 20, red lamp 23R, yellow lamp 23Y, green lamp 23G, and other electronics are mounted within the metal box 32. The metal cover plate 34 has a cut-out portion covered with the mesh or screen 38 of thin copper wires. The wires forming the copper mesh 38 are thin enough so that the images from the display panel 20 are not obstructed but rather are clearly visible by the patient P. The lamps 23R, 23Y, and 23G are also covered by copper mesh mounted to the cover plate 34 with brass rings 37.

The cover plate 34 is mounted to the front of the metal box 32 with the RFI gasket 36 placed therebetween. The RFI gasket, the metal box 32, the cover plate 33, and the copper mesh 38 form a Faraday shield to completely shield the MRI device from any fields generated by the display panel 20, lamps 23, and other electronics and to shield the components within the enclosure 28 from the fields generated by the MRI device. A magnetic shield 39 may be used to house components which are especially sensitive to strong magnetic fields.

The foregoing description of the preferred embodiment of the invention has been presented for purposes of illustration and description. It is not intended to be exhaustive or to limit the invention to the precise form disclosed. Many modifications and variations are possible in light of the above teaching.

For example, while the invention has been described in conjunction with an MRI device, the invention may be used with other equipment or in other environments, such as in a dental office or with out-patient surgery. Further, an intercom system may be incorporated with the audio portion of the entertainment system to provide a channel of communication between the patient P and the MRI operator. Further, the remote control unit 38 may have a greater or lesser number of buttons.

Also, when the MRI computer interface 44 is used, additional features or items may be displayed on the display panel 20. For instance, the MRI computer interface 44 may receive data indicating the amount of time remaining in the MRI procedure. The amount of time may be displayed on the display panel 20 as a 100% bar graph which is reduced in size and in rate according to the percentage of time which has elapsed. When the MRI procedure is completed, the bar graph is reduced to zero and the green lamp 23G is lit. Alternatively, the amount of time remaining may be indicated in minutes and seconds on the display panel 20 and will count down to zero at which time the green lamp 23G will be lit. With either alternative, the display of time will have the same orientation as the video image whereby the remaining time can always be correctly viewed by the patient P. The two alternatives may be user selectable, such as by depressing another button on the remote control unit 38.

It should be understood that the display panel 20 can project images which are not intended to merely entertain the patient P. For example, the display panel 20 may have commercial advertisements instead of or in addition to images displayed on the panel 20 intended to distract and entertain the patient P. Further, the display panel 20 may be used in studies of brain activity which require visual stimulus, such as an image, a message to be read, or a problem to be solved. The display panel 20 therefore permits the "functional imaging" of a patient P.

The embodiment was chosen and described in order to explain the principles of the invention and their practical application to thereby enable others skilled in the art to utilize the invention and various embodiments and with various modifications as are best suited to the particular use contemplated. It is intended that the scope of the invention be defined by the claims.

Wherefore, the following is claimed:

1. An arrangement for entertaining a patient within a magnetic resonance imaging device, comprising:
   a magnetic resonance imaging device in an examination room;
   a patient positioned within said magnetic resonance imaging device;
   a video display panel having a video display screen, said video display panel being positioned in said examination room within a magnetic field generated by said magnetic resonance imaging device, said patient being capable of direct viewing of said video display screen;
   an image generated on said display screen to entertain said patient;
   a mirror disposed within said magnetic resonance imaging device, said patient being capable of viewing a direct reflection of said display screen in said mirror without fiber optic coupling; and
   a magnetically shielded enclosure integral to said video display panel, said enclosure shielding said magnetic resonance imaging device from an internal magnetic field generated in said video display panel, and said enclosure shielding said video display from an external magnetic field generated by said magnetic resonance imaging device, said magnetically shielded enclosure having a metal box with an open face, a cover plate with a cut-out for the video display screen, said cover plate fastened to said metal box, a radio frequency interference gasket to seal the joint said metal box and said cover plate, and a wire mesh covering said cut-out in said plate.

2. The arrangement of claim 1, wherein said image generated on said display screen is displayed in a normal viewing orientation when said patient is in a headfirst, prone position for direct viewing by said patient, said image being reversed from left to right when said patient is in a head-first supine position viewing a reflection of said display screen on said mirror, said image being reversed from top to bottom when said patient is in a head-first supine position for direct viewing by said patient, and said image being reversed from left to right and from top to bottom when said patient is in a feet-first supine position viewing a reflection of said display screen on said mirror.

3. The arrangement of claim 1, wherein said cover plate further comprises at least one hole for a viewing lamp, said hole covered by a second wire mesh mounted to said cover plate with a brass ring, said wire mesh constructed from thin wires allowing the viewing of said lamp without obstruction.

4. The arrangement of claim 1, further comprising at least one sensitive electrical component effected by strong magnetic fields disposed within said video display panel, said sensitive electrical component being housed within an internal metal electromagnetic shield.

5. The arrangement of claim 1, wherein said wire mesh is constructed from a plurality of thin wires allowing the viewing of said video images without obstruction.

6. A method of shielding a video display to prevent electromagnetic interference with a magnetic resonance imaging device located in proximity to said video display, comprising the steps of:
   (a) positioning a patient within a magnetic resonance imaging device disposed in an examining room;
   (b) examining said patient with said magnetic resonance imaging device;
   (c) placing a video display panel in said examining room within a magnetic field generated by a magnetic resonance imaging device and within direct viewing range of said patient;

(d) producing a video image on a video display screen within said video display panel;

(e) orienting said video image on said video display screen in relation to an orientation of said patient within said magnetic resonance imaging device;

(f) reflecting said video image from said display screen to said patient using a mirror without a fiber optic coupling; and (g) shielding said video display panel within a magnetic shielding enclosure, said enclosure shielding said magnetic resonance imaging device from an internal magnetic field generated by said video display, and said enclosure shielding said video display panel from an external magnetic field generated by said magnetic resonance imaging device, wherein the step of shielding said video display panel comprises the steps of:

(1) enclosing said video display in a metal box with an open face;

(2) closing said open face with by fastening a cover plate with a cut-out for a viewing screen to said metal box;

(3) sealing the joint between said metal box and said cover plate with a radio frequency interference gasket; and (4) covering said cut-out in said cover plate with a wire mesh.

7. The method of claim 6, wherein the step of orienting said video image on said video display screen further comprises the step of:

displaying said image in a normal viewing orientation when said patient is in a head-first, prone position for direct viewing by said patient, displaying said image reversed from left to right when said patient is in a head-first supine position, said patient viewing a reflection of said display screen on said mirror;

displaying said image reversed from top to bottom when said patient is in a head-first supine position for direct viewing by said patient; and displaying said image reversed from left to right and from top to bottom when said patient is in a feet-first supine position viewing a reflection of said display screen on said mirror.

8. The method of claim 6, wherein said step of shielding said video display panel further comprises the step of (5) displaying at least one viewing lamp through a hole in said cover plate;

(6) covering said hole with a second wire mesh mounted to said cover plate, with a brass ring, said second wire mesh constructed from thin wires allowing the viewing of said viewing lamp without obstruction.

9. The method of claim 6, further comprising the step of shielding a sensitive electrical component inside said video display panel with an internal electromagnetic shield.

* * * * *